(12) United States Patent
Tsai et al.

(10) Patent No.: US 7,741,496 B2
(45) Date of Patent: Jun. 22, 2010

(54) ASCORBIC ACID DERIVATIVES

(75) Inventors: Wei-Chuan Tsai, Taipei (TW); Chen-Yin Chen, Taipei (TW); Ming-Yi Chiu, Taipei (TW); Yi-Fan Ling, Taipei (TW); Nai-Hsuan Hsu, Taipei (TW)

(73) Assignee: Corum Inc., Taipei (TW)

( * ) Notice: Subject to any disclaimer, the term of this patent is extended or adjusted under 35 U.S.C. 154(b) by 0 days.

(21) Appl. No.: 12/553,220

(22) Filed: Sep. 3, 2009

(65) Prior Publication Data

US 2010/0056809 A1    Mar. 4, 2010

Related U.S. Application Data

(60) Provisional application No. 61/094,245, filed on Sep. 4, 2008.

(51) Int. Cl.
*C07D 307/33* (2006.01)

(52) U.S. Cl. .................................................. 549/315

(58) Field of Classification Search ................ 549/315
See application file for complete search history.

(56) References Cited

U.S. PATENT DOCUMENTS

2008/0287533 A1* 11/2008 Gupta ........................ 514/474

* cited by examiner

*Primary Examiner*—Janet L Andres
*Assistant Examiner*—David E Gallis
(74) *Attorney, Agent, or Firm*—WPAT, PC; Justin King

(57) ABSTRACT

The present invention discloses the ascorbic acid derivatives. The inventive molecules that combine with one or two hydrophilic headgroups connected by a hydrophobic spacer can increase skin penetration.

6 Claims, 2 Drawing Sheets

ASCORBIC ACID DERIVATIVES

BACKGROUND OF THE INVENTION

1. Field of the Invention

The invention relates to cosmetic compositions, such compositions in order to inhibiting darkening of the skin and initiates the stimulation of collagen synthesis.

Azelaic acid may be used as therapeutic agent in the treatment of skin disorders and also have whiting effect. Azelaic acid is very polar due to the two carboxyl groups. Because of this polarity, skin penetration is very low. The inventive molecules that combine with one or two hydrophilic headgroups connected by a hydrophobic spacer can increase skin penetration.

Enzymatic synthesis is widely using in various industrial scopes such as cosmetics, fine chemicals, pharmaceuticals and food ingredients. Lipase-catalyzed reactions are superior to conventional chemical methods owing to mild reaction conditions, high catalytic efficiency and the inherent selectivity of natural catalysts, which results in much purer products.

2. Description of the Prior Art

L-ascorbic acid is a well-know water-soluble antioxidant that has whitening effect and serves as a cofactor of proline-hydroxylase to promote synthesis of collage (Quaglino, D. Jr., et al., J. Biol. Chem., p 272-345, 1997). L-ascorbic acid is also used in various products requiring a long-term antioxidation effect. But its unfulness for such products is not so reliable because it is sensitive to heat light and air. As a result, many studies have been made on the development of ascorbic acid derivatives with enhanced stability while maintaining the antioxidation activity. Notably, a common way to improve the stability of L-ascorbic acid is converting a 2- or 3-hydroxyl group of L-ascorbic acid to another subsistent (U.S. Pat. No. 6,444,144; 5,143,648; 4,780,549; and 4,177,455, Japan Pat. Sho 52-18191, and Korean Pat. No. 91-8733).

The novel ascorbic acid derivative 3-O-ethyl-ascorbic acid is a structurally stabile ascorbic acid and effective whitening agent that can it the polymerization arising due to the biological dihydroxyindole in vivo caused by ultraviolet rays (U.S. Pat. No. 6,861,050). This novel ascorbic acid derivative is metabolized by the human body in the same manner as regular ascorbic acid and it's soluble in water as well as oil, making it optimal for use in cosmetics.

Azelaic acid is a naturally occurring nine carbon straight chain molecule with two terminal carboxyl groups. Azelaic acid is an anti-keratinizing agent, displaying antiproliferative effects on keratinocytes and modulating the early and terminal phases of epidermal differentiation (Passi, et al. G. Ital. Dermatol. Venerol. 1989, 124(10):455-463). Azelaic acid is a competitive inhibitor of the reduction of testosterone to dihydrotestosterone, and as such is supposed to reduce the production of sebum in the sebaceous gland. Furthermore, recent investigations gave demonstrated that azelaic acid and seba-structure-activity relationship studies gave revealed that these effects are retained when the dicarboxylic acid has a backnone of about 2 to 10 carbons (U.S. Pat. No. 6,180,669).

SUMMARY OF THE INVENTION

According to the background of this application, the ascorbic acid derivatives are disclosed, wherein the ascorbic acid derivatives compound has a general formula as following:

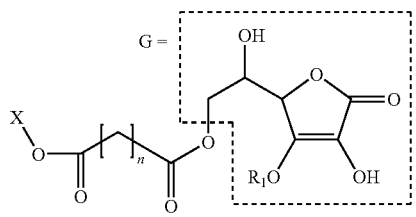

wherein X is selected from the group consisting one of the following the G group, hydrogen, linear alkyl moiety, branched alkyl moiety, cyclic alkyl moiety; n ranges from 2 to 12; and $R_1$ is selected from the group consisting one of the following: hydrogen, alkyl group having 1 to 4 carbon, linear alkyl moiety, branched alkyl moiety.

The invention also provides other ascorbic acid derivatives, wherein the ascorbic acid derivatives compound has a general formula as following:

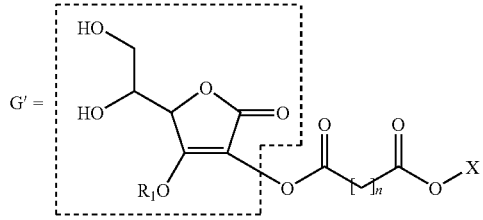

wherein X is selected from the group consisting one of the following: the G' group, hydrogen, linear alkyl moiety, branched alkyl moiety, cyclic alkyl moiety; n ranges from 2 to 12; and $R_1$ is selected from the group consisting one of the following: hydrogen, alkyl group having 1 to 4 carbon, linear alkyl moiety, branched alkyl moiety.

DESCRIPTION OF THE PREFERRED EMBODIMENTS

What is probed into the invention is ascorbic acid derivatives. Detail descriptions of the structure and elements will be provided as followed in order to make the invention thoroughly understood. The application of the invention is not confined to specific details familiar to those who are skilled in the art. On the other hand, the common structures and elements that are known to everyone are not described in details to avoid unnecessary limits of the invention. Some preferred embodiments of the present invention will now be described in greater detail as followed. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

Figure 1:
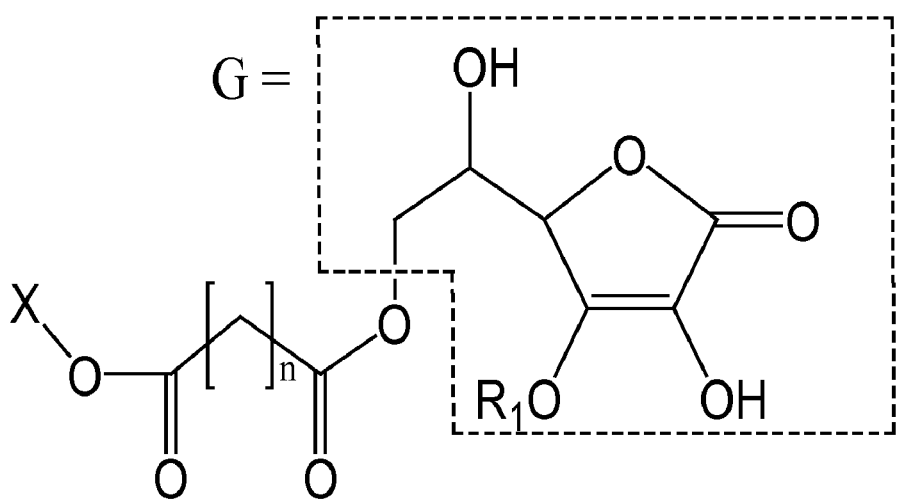
FIG. 1 is a formula of the ascorbic acid derivatives to the first embodiment of the present invention.

As shown in FIG. 1, the first embodiment of the invention discloses ascorbic acid derivatives, wherein the ascorbic acid derivatives compound has a general formula as following:

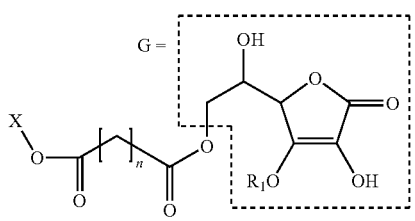

wherein X is selected from the group consisting one of the following: the G group, hydrogen, linear alkyl moiety, branched alkyl moiety, cyclic alkyl moiety; n ranges from 2 to 12; and $R_1$ is selected from the group consisting one of the following: hydrogen, alkyl group having 1 to 4 carbon, linear alkyl moiety, branched alkyl moiety.

The first example of the first embodiment of the invention discloses ascorbic acid derivatives, wherein formula of said ascorbic acid derivatives is

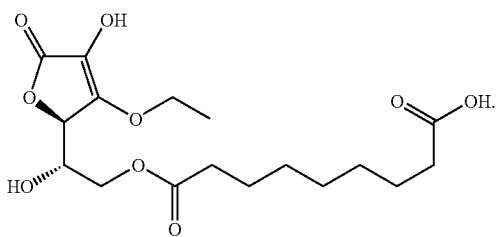

The second example of the first embodiment of the invention discloses ascorbic acid derivatives, wherein formula of said ascorbic acid derivatives is

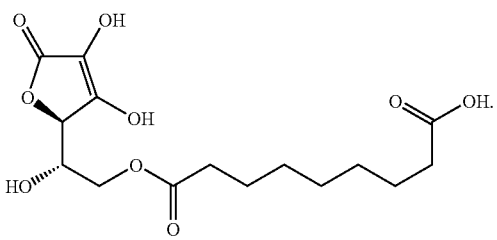

Figure 2:
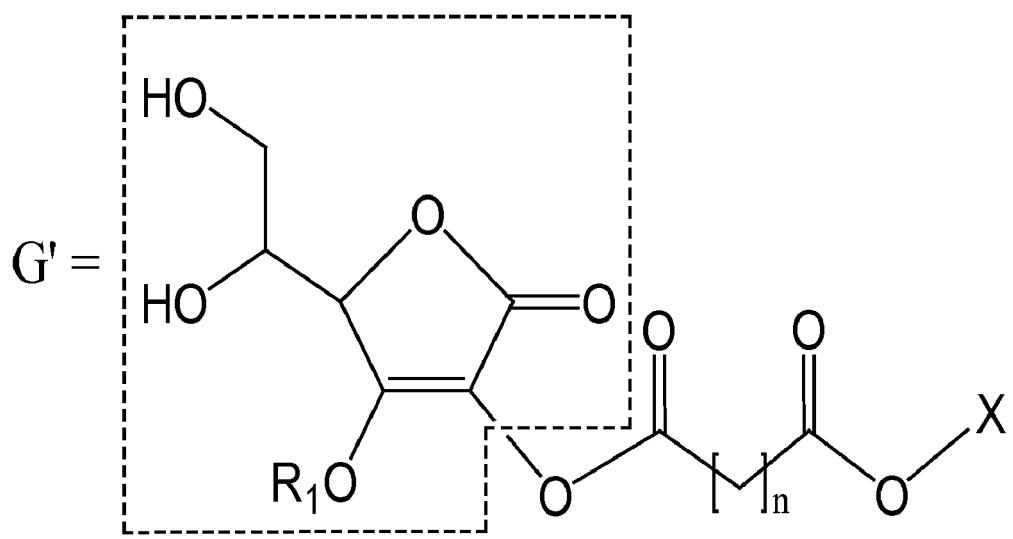
FIG. 2 is a formula of the ascorbic acid derivatives to the second embodiment of the present invention.

As shown in FIG. 2, the second embodiment of the invention discloses ascorbic acid derivatives, wherein the ascorbic acid derivatives compound has a general formula as following:

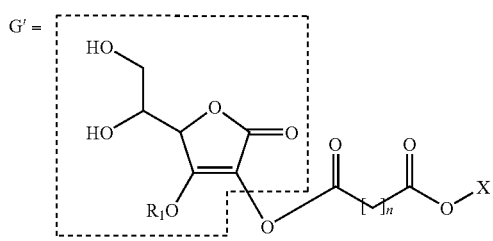

wherein X is selected from the group consisting one of the following: the G' group, hydrogen, linear alkyl moiety, branched alkyl moiety, cyclic alkyl moiety; n ranges from 2 to 12; and $R_1$ is selected from the group consisting one of the following: hydrogen, alkyl group having 1 to 4 carbon, linear alkyl moiety, branched alkyl moiety.

The first example of the second embodiment of the invention discloses ascorbic acid derivatives, wherein formula of said ascorbic acid derivatives is

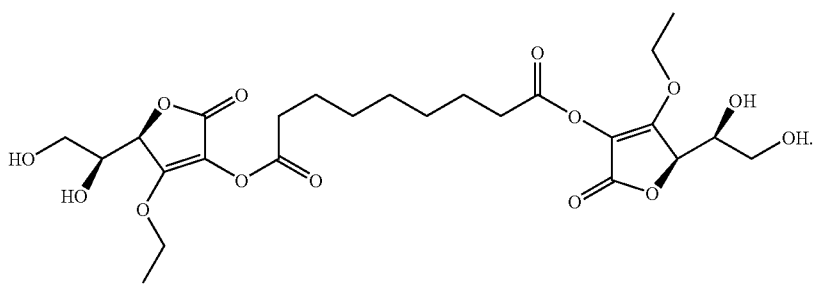

The second example of the second embodiment of the invention discloses ascorbic acid derivatives, wherein formula of said ascorbic acid derivatives is

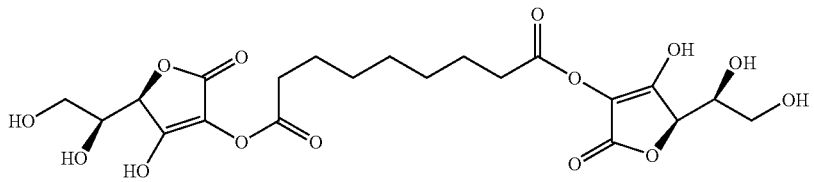

EXAMPLE

Best Mode For Carrying Out the Invention

Formula (I)

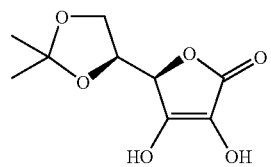

Preparation Example 1

Synthesis of 5, 6-O-isopropylidene-L-ascorbic acid (Formula I)

Methanesulfonic acid (13 mL, 0.200 mol) was dropwised to slurry of L-ascorbic acid (10 g, 0.568 mol) in acetone (400 mL). The mixture was stirred at 25-30° C. After 5 hours, the crystalline product separated. The crystals were collected by filtration, washed with cool acetone and dried in vacuum desiccators at 40° C. Gave 100 g of Formula I (0.463 mol; yield 80%).

Formula (II)

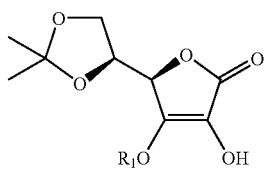

Formula (III)

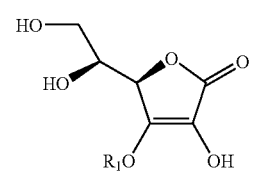

Preparation Example 2

Synthesis of -3-O-ethyl-L-ascorbic acid

Formula I (10 g, 0.465 mol) was dissolved in 172 mL of dimethylformamide and then sodium bicarbonate (102 g, 1.605 mol) was added, followed by addition of ethyl tosylate (81 g, 0.404 mol), nitrogen was in purged. The reaction mixture was stirred at 60° C. for 10 hours. After cooled to the room temperature, sodium bicarbonate and salt were filtered and evaporated. After evaporation, 5% sodium bicarbonate (100 mL) was added into crude and extracted for twice with Toluene. The organic phase was washed with water and evaporated. Crystallization from n-heptane gave 55 g formula II (0.225 mol; yield=65%). Intermediate was dissolved in n-propanol (60 mL) and then added 2N HCl (16.9 mL), heat to 60° C., after 2 hours, the solvent was evaporated. re-crystallization from Toluene and n-propanol gave 35 g of formula (III). (0.172 mol; yield 56%)

Formula (IV)

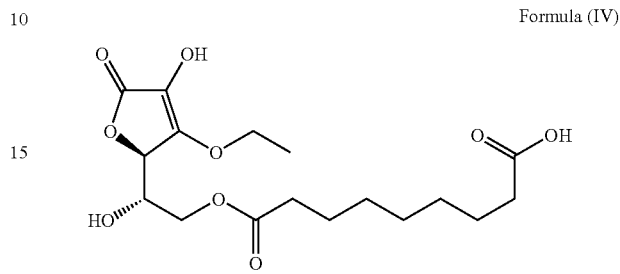

Example 1

Synthesis of 3-O-ethyl-ascorbyl-6-nonanedioate

3-O-ethyl-ascorbic acid (1.19 g, 5.851 mmol) and azelaic acid (1 g, 5.319 mmol) were dissolved in 10 mL tert-amyl alcohol and heat to 55° C. Lipase (0.3 g) was added into reaction mixture. The reaction solution was stirred for 18 hours at 55° C. and then evaporated solvent. Extracted with ethyl acetate and washed with water, dried with magnesium sulfate and evaporated. The product was purified on silica gel column, to yield 0.65 g (1.74 mmol, yield 32.7%). The compound was characterized by NMR: 1.25-1.53, m, 13H; 2.0, s, 1H; 2.16-2.32, t, 4H; 4.02-4.47, m, 5H; 5.3, d, 1H; 8.66, s, 1H; 11.94, s, 1H Formula (V)

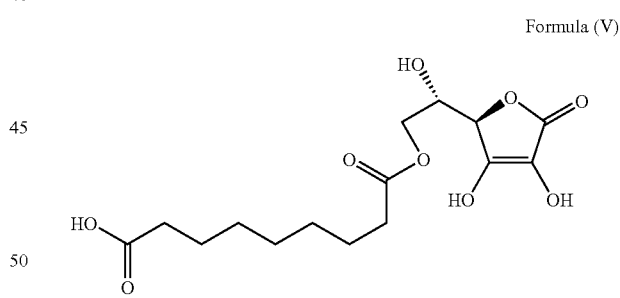

Example 2

Synthesis of Ascorbyl-6-nonanedioate

Ascorbic acid (1.03 g, 5.851 mmol) and azelaic acid (1 g, 5.319 mmole) were dissolved in 10 mL tera-amyl alcohol and 5 mL N-methyl-2-Pyrrolidone. Lipase (0.3 g) was added into reaction mixture. The reaction solution was stirred for 24 hours at 55° C. and then evaporated solvent. Extracted with ethyl acetate and washed with water, dried with magnesium sulfate and evaporated (purity 91.8%). The compound was characterized by Mass: mw. 346

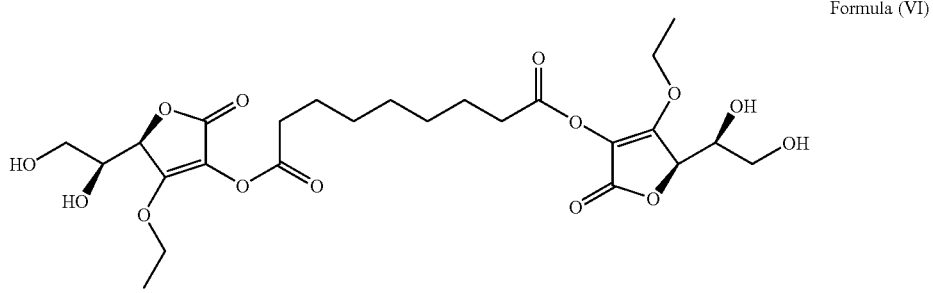

Formula (VI)

Example 3

Synthesis of 2,2-O-nonanedioyl-di-3-O-ethyl-ascorbate

Formula II (4.55 g, 1.865 mmol) was dissolved in 80 mL Tertrahydrofuran. Azelaoyl chloride (2 g, 0.888 mmol) and triethylamine (1.1 g, 1.954 mmol) were dropped respectively with ice bath (5-10° C.). The reaction mixture was stirred for 1 hour at 5-10° C. and then tertrahydrofuran was evaporated. The residue was extracted for twice by toluene/H2O and evaporated to obtain 5 g (Intermediate I; 7.813 mmol; yield=84%). Intermediate I (5 g, 7.813 mmol) was dissolved in 25 mL methanol then poured into 2N HCl (0.5 mL). The reaction mixture was stirred at 40° C. for 12 hours and evaporated. The product was purified on a silica gel column to yield 2 g (3.571 mmol; yield=38%).

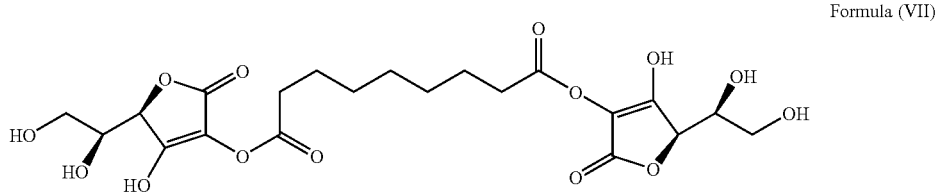

Formula (VII)

Example 4

Synthesis of 2,2-O-nonanedioyl-di-ascorbate

The 10 g (0.046 mol) of Formula (I) was dissolved in 120 g dichloromethane. 15.5 g (0.154 mol) of triethylamine was added. The temperature was set at 5-10° C. Azelaoyl chloride (5 g, 0.022 mol) was dropwise into reactor and than was stirred at 5-10° C. 1 hr. The mixture solution was extracted by 10 mL triethylamine/50 mL H2O. The organic layer was discarded. Add 6 mL TFA/H2O solution to water layer to adjust pH to 3-4 and than water layer was extracted by dichloromethane twice. Dichloromethane was evaporated at 40° C. to give white solid intermediate I. (Purity=90.6%, weight=10.76 g). Intermediate I (10 g, 0.018 mol) of was dissolved in 50 mL dichloromethane. Trifluoroacetic acid (1 mL, 0.019 mol) was slowly dropped into the mixture. The mixture was stirred at 25° C. overnight and then the crude mixture was evaporated by vacuum. The product was purified on a silica gel column to yield 4.5 g (8.929 mmol; yield=40.9%). The compound was characterized by Mass: mw.504

Experiment Design:

Preparation

L-Dopa (L-3,4-dihydroxyphenylalanine) (2 mg/mL) and Tyrosine (0.083 mg/mL) were dissolved in pH6.5 buffer solution. Samples were dissolved in water and prepared at 1% concentration.

Method:

1 mL L-Dopa solution was added into 1 mL sample solution (or blank solution) and measured by thermo spectronic 475 nm ($A_{so}$ or $A_{b0}$). 250 μl tyrosine solution was added into mixture. After reaction for 3 min, mixture was measured by thermo spectronic ($A_{s3}$ or $A_{b3}$).

Calculation $$\% \text{ Inhibition} = 100 \times \frac{(A_{b3} - A_{b0}) - (A_{s3} - A_{s0})}{(A_{b3} - A_{b0})}$$

Figure 3:
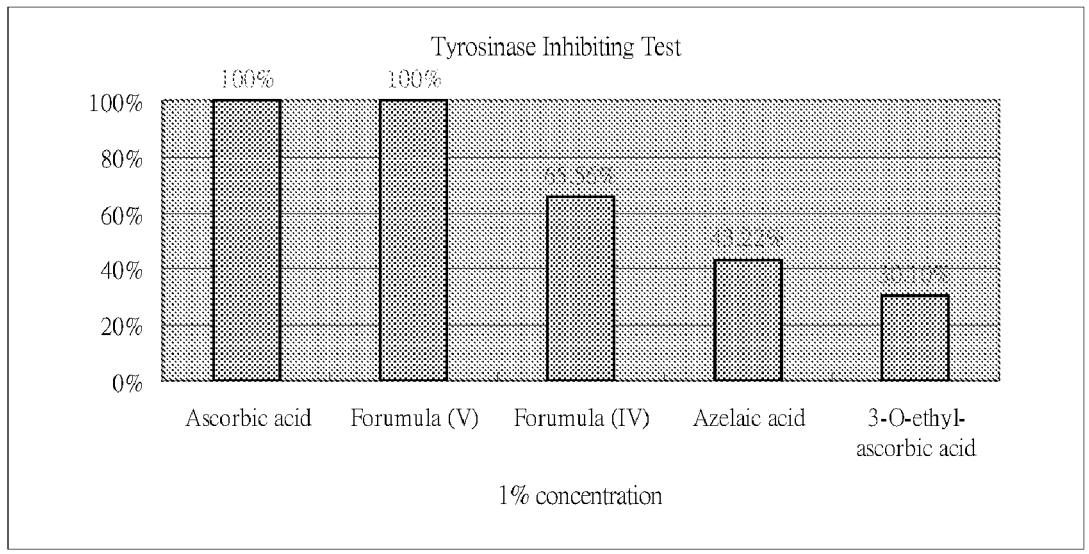
FIG. 3 is a diagram of Tyrosinase Inhibiting Test.
Figure 4:
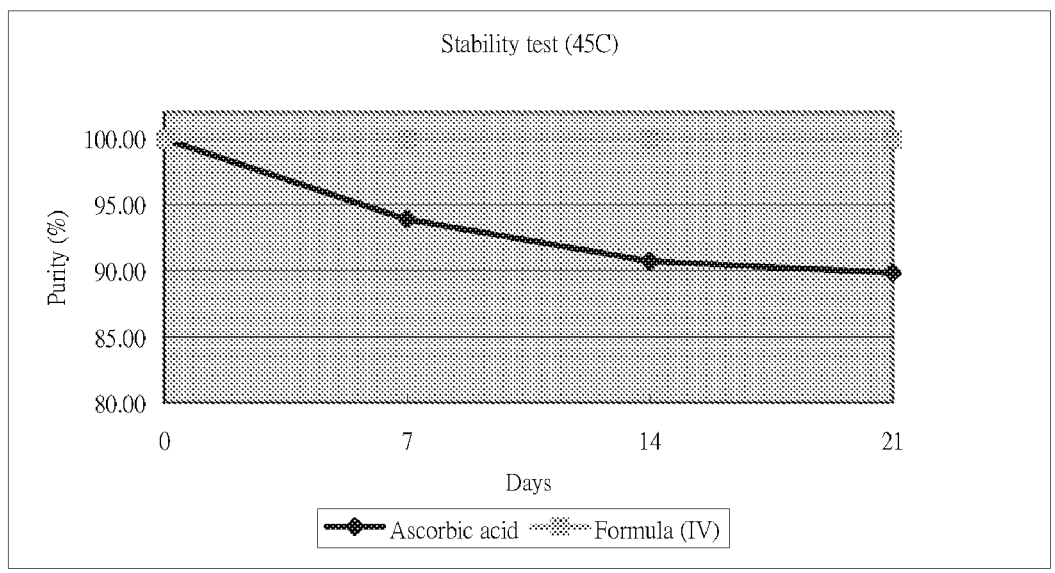
FIG. 4 is a diagram of Thermal Stability Test observed at 45° C. oven for 21 days.

As shown in FIG. 3, the result of Tyrosinase Inhibiting Test. Competitive with 3-O-ethyl-ascorbic acid and Azelaic acid, inventive samples have best effect in tyrsoinase inhibition. As shown in FIG. 4, in thermal stability test, samples are observed at 45° C. oven for 21 days. Show Formula (IV) was stable than ascorbic acid.

Other modifications and variations are possibly developed in light of the above demonstrations. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

Ascorbic Acid derivative reference:

U.S. Pat. No. 4,179,445
U.S. Pat. No. 4,999,437
U.S. Pat. No. 5,084,563
U.S. Pat. No. 5,143,648
U.S. Pat. No. 4,780,549
U.S. Pat. No. 4,177,445
U.S. Pat. No. 6,444,144 B1
U.S. Pat. No. 6,180,669 B1

WO 9917714
WO 2007003289
International Journal of Dermatology, December 1991, pages 893-895
Journal of the American Academy of Dermatology, May 2006, supplemental, pages 272-281

What is claimed is:

1. An ascorbic acid derivative, wherein the ascorbic acid derivative has a general formula as following:

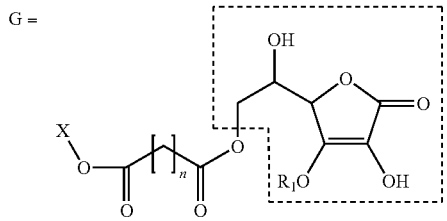

wherein X is selected from the group consisting one of the following the G group, hydrogen, linear alkyl moiety, branched alkyl moiety, cyclic alkyl moiety;
n ranges from 2 to 12; and
$R_1$ is selected from the group consisting one of the following: hydrogen, alkyl group having 1 to 4 carbon, linear alkyl moiety, branched alkyl moiety.

2. The ascorbic acid derivative of claim 1, wherein formula of said ascorbic acid derivative is

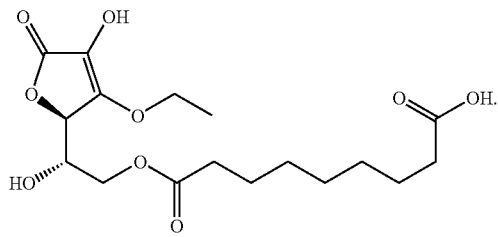

3. The ascorbic acid derivative of claim 1, wherein formula of said ascorbic acid derivative is

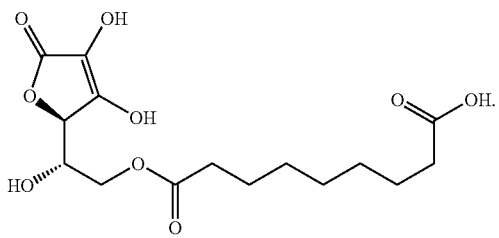

4. An ascorbic acid derivative, wherein the ascorbic acid derivatives has a general formula as following:

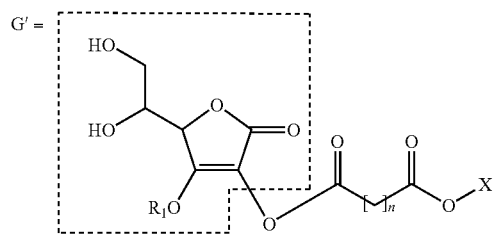

wherein X is selected from the group consisting one of the following:
the G' group, hydrogen, linear alkyl moiety, branched alkyl moiety, cyclic alkyl moiety;
n ranges from 2 to 12; and
$R_1$ is selected from the group consisting one of the following: hydrogen, alkyl group having 1 to 4 carbon, linear alkyl moiety, branched alkyl moiety.

5. The ascorbic acid derivative of claim 4, wherein formula of said ascorbic acid derivative is

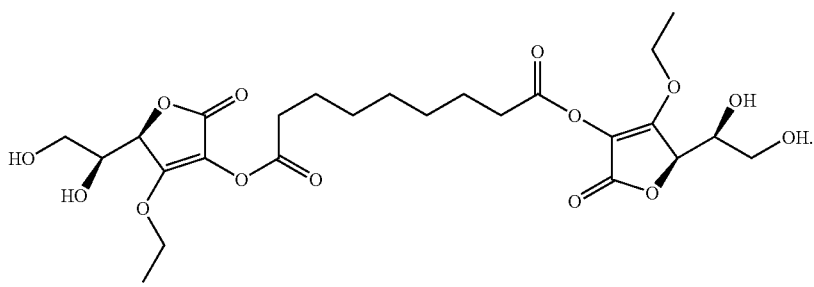

6. The ascorbic acid derivative of claim 4, wherein formula of said ascorbic acid derivative is

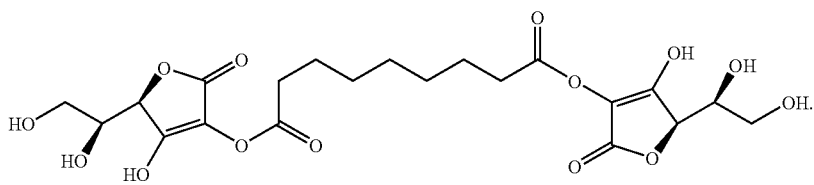

* * * * *